(12) United States Patent
Habibi et al.

(10) Patent No.: US 11,672,626 B2
(45) Date of Patent: Jun. 13, 2023

(54) MARKER FOR IDENTIFYING SURGICAL CAVITY IN TARGETED RADIATION

(71) Applicant: The Johns Hopkins University, Baltimore, MD (US)

(72) Inventors: Mehran Habibi, Perry Hall, MD (US); Farhad Shir, Ashburn, VA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/302,942

(22) Filed: May 17, 2021

(65) Prior Publication Data

US 2021/0275276 A1    Sep. 9, 2021

Related U.S. Application Data

(63) Continuation of application No. PCT/US2019/062042, filed on Nov. 18, 2019.

(60) Provisional application No. 62/769,259, filed on Nov. 19, 2018.

(51) Int. Cl.
*A61B 90/00* (2016.01)
*A61B 90/94* (2016.01)
*A61B 6/02* (2006.01)

(52) U.S. Cl.
CPC .............. *A61B 90/39* (2016.02); *A61B 6/02* (2013.01); *A61B 90/94* (2016.02); *A61B 2090/3762* (2016.02); *A61B 2090/3912* (2016.02); *A61B 2090/3966* (2016.02)

(58) Field of Classification Search
CPC .......... A61B 90/39; A61B 90/92; A61B 90/94
See application file for complete search history.

(56) References Cited

U.S. PATENT DOCUMENTS

| 5,405,402 | A | * | 4/1995 | Dye | A61F 2/30724 |
|---|---|---|---|---|---|
| | | | | | 623/22.38 |
| 7,123,690 | B1 | * | 10/2006 | Brown | A61B 90/39 |
| | | | | | 378/165 |
| D634,011 | S | * | 3/2011 | Phillips | D8/395 |
| 9,610,432 | B2 | * | 4/2017 | Zinn | A61M 39/0208 |
| 10,342,664 | B2 | * | 7/2019 | Kieser | A61B 90/98 |
| 2004/0052333 | A1 | * | 3/2004 | Sayre | A61B 90/39 |
| | | | | | 378/163 |

(Continued)

FOREIGN PATENT DOCUMENTS

| WO | 2010141422 A1 | 12/2010 |
|---|---|---|
| WO | 2018045465 A1 | 3/2018 |

(Continued)

OTHER PUBLICATIONS

Search Report and Written Opinion for Application No. PCT/US2019/062042, dated Feb. 20, 2020, 6 pages.

(Continued)

*Primary Examiner* — Angela M Hoffa
*Assistant Examiner* — Younhee Choi
(74) *Attorney, Agent, or Firm* — Harrity & Harrity, LLP

(57) ABSTRACT

A marker for identifying a portion of a surgical margin includes a first element to attach the marker to the surgical margin of a surgical cavity located in a body of a patient, and a second element attached to the first element. The second element includes an indicator to uniquely identify the portion of the surgical margin through a radiological scan.

29 Claims, 7 Drawing Sheets

(56) References Cited

U.S. PATENT DOCUMENTS

| | | | |
|---|---|---|---|
| 2006/0173296 A1* | 8/2006 | Miller | A61B 90/39 600/431 |
| 2008/0188768 A1* | 8/2008 | Zarins | A61B 90/39 600/567 |
| 2012/0083804 A1* | 4/2012 | Skerven | A61B 17/10 606/142 |
| 2012/0226146 A1* | 9/2012 | Schwartz | A61B 90/98 359/871 |
| 2015/0065362 A1 | 3/2015 | Gyorffy et al. | |
| 2015/0112117 A1 | 4/2015 | Stubbs et al. | |
| 2019/0054292 A1* | 2/2019 | Muessig | A61N 1/37518 |
| 2021/0169579 A1* | 6/2021 | Laviola | A61B 8/481 |

FOREIGN PATENT DOCUMENTS

| | | |
|---|---|---|
| WO | 2018097891 A1 | 5/2018 |
| WO | 2020106634 A1 | 5/2020 |

OTHER PUBLICATIONS

Extended European Search Report for Application No. EP19887914.0, dated Jul. 25, 2022, 10 pages.

* cited by examiner

MARKER FOR IDENTIFYING SURGICAL CAVITY IN TARGETED RADIATION

RELATED APPLICATION

This application is a continuation of International Application No. PCT/US/2019/062042, filed on Nov. 18, 2019, and entitled "Marker for Identifying a Surgical Cavity", which claims priority under 35 U.S.C. § 119 to U.S. Provisional Patent Application No. 62/769,259, filed on Nov. 19, 2018, and entitled "Marker for Identifying Portions of a Surgical Margin of a Surgical Cavity," the contents of which are incorporated by reference herein in their entireties.

BACKGROUND

Treatment modalities for cancer include tumor resection (e.g., from a lung, pancreas, prostate, bladder, breast, trachea, and/or the like), systemic therapy with hormone therapy, radiation therapy, and/or the like. When performing post-resection treatment, such as radiation therapy, identifying a location of target tissue in a post-surgical cavity is important, so that a guided treatment can be performed on the target tissue without harming surrounding tissues.

DETAILED DESCRIPTION

Figure 1:
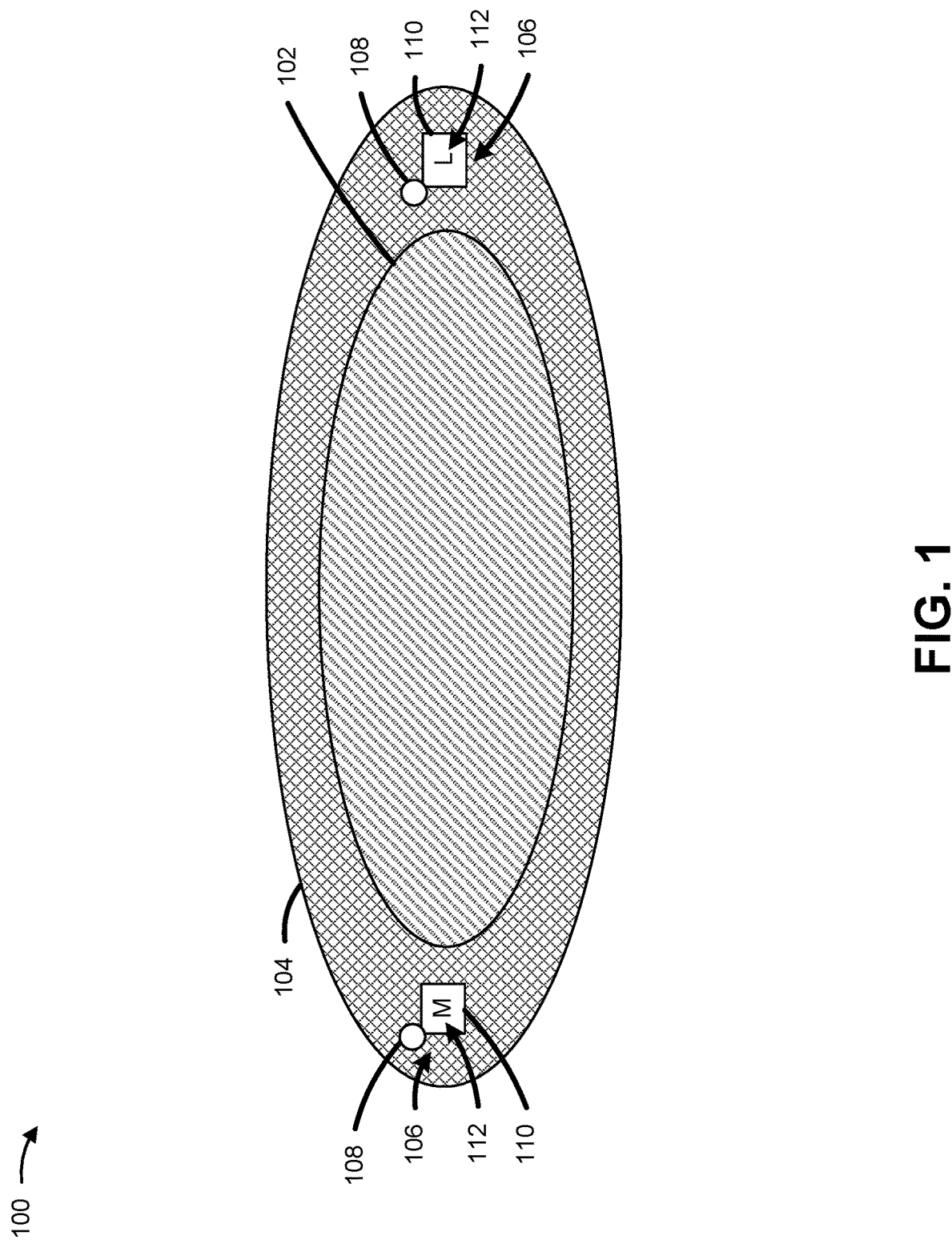
FIG. 1 is an illustration of an example implementation described herein.

The following detailed description of example implementations refers to the accompanying drawings. The same reference numbers in different drawings may identify the same or similar elements.

When a tumor is resected, an abnormal tissue is removed from a patient's body, which results in a surgical cavity. After the resection, the treating surgeon may re-approximate one or more of the borders of the cavity, may move the borders of the resection, and/or may relocate tissue from the areas surrounding the cavity to fill the cavity. For example, during or after a lumpectomy or a partial mastectomy, the treating surgeon may perform reconstructive surgery on the breast tissue, which may move the borders of the resection, may relocate tissue from the areas surrounding the cavity, and/or the like, making the borders of the resection difficult to identify.

After the abnormal tissue is removed, a pathologist performs an assessment of the surgical margin of the surgical cavity to determine whether the surgical margin surrounding the surgical cavity is free of the abnormal tissue. In the case of positive margin at any of the borders, the treating surgeon may choose to go back for the resection of that particular margin. Once all margins are cleared, a radiation oncology practitioner may attempt to identify the surgical margin of the surgical cavity using a computed tomography (CT) simulation of the surgical cavity, and may plan radiation treatment to target rays of radiation on the tissue surrounding the surgical cavity. Given the possibility of tissue transfer during the resection (e.g., during re-approximation of the borders of the cavity, movement of the borders of the resection, and/or the like), areas identified as the surgical margin by the CT simulation may not accurately represent the actual borders of the surgical margin. Furthermore, various techniques for marking the surgical margins of a surgical cavity may be utilized, but such techniques tend to be difficult and unreliable. For example, surgical clips that are typically used for sealing off small blood vessels may be used, but surgical clips lack individualization for marking individual portions of a surgical margin and may also be used for hemostasis purposes but be mistaken for a surgical margin.

Some implementations described herein provide a marker for identifying portions of a surgical margin of a surgical cavity. In some implementations, the surgical margin may be a particular surgical margin, such as an anterior portion of a surgical margin, a posterior portion of a surgical margin, a lateral portion of a surgical margin, a medial portion of a surgical margin, a superior portion of a surgical margin, an inferior portion of a surgical margin, and/or the like. An indicator on the marker may include an alphabetical letter or other type of indicator that represents the portion of the surgical margin. Depending on the type of abnormal tissue associated with the surgical cavity, and the location of the surgical cavity in the patient (e.g., a bronchial surgical cavity, a tracheal surgical cavity, a bladder surgical cavity, a pancreatic surgical cavity, a prostate surgical cavity, and/or the like), other types of indicators may be used to identify the significance of the surgical margin.

In some implementations, the surgical margin may be associated with a surgical cavity, such as a lumpectomy cavity, a complete or partial mastectomy cavity, an excisional biopsy in breast surgery, and/or the like. In some implementations, the surgical cavity may be associated with another type of surgical intervention in which identifying the exact location of the surgical margin is desirable, including, but not limited to pancreas surgery, liver surgery, lung surgery, prostate surgery, and/or the like.

In some implementations, the marker may include a first element to attach the marker to a portion of a surgical margin associated with a surgical cavity of a patient, and a second element attached to the first element, wherein the second element includes an indicator to uniquely identify the portion of the surgical margin through a radiological scan, such as a CT scan and/or the like. In this way, the indicator identifies a location of the portion of the surgical margin relative to the surgical cavity. Further, the indicator distinguishes a portion of the surgical margin relative to other portions of the surgical margin of the surgical cavity.

In some implementations, the first element may include at least one protrusion projecting from the second element and penetrating into a body tissue of the patient. The at least one protrusion may irreversibly deform to attach the marker to the body tissue of the patient. In some implementations, the first element may include a hollow portion for receiving a thread that may be used to stitch the marker to the body tissue of the patient. The first element may be an integral part of the second element such that the first element and the second element are a single piece, the first element and the second element are separate pieces that are removably attachable, and/or the like.

Some implementations described herein provide a plurality of markers for identifying portions of a surgical margin of a surgical cavity. Each marker, of the plurality of markers, includes a first element for attachment to a body tissue of the patient, and a second element attached to the first element and including an indicator. Each marker, of the plurality of markers, may correspond to a particular portion, of the plurality of portions, of the surgical margin. Each marker, of the plurality of markers, may be different from the remaining markers of the plurality of markers such that each of the markers is independently distinguishable from the remaining markers through a radiological scan. In this way, each of the markers uniquely identifies a portion of the surgical margin in the radiological scan.

In some implementations, the indicator of the second element of a particular marker may include a different shape, may include a different alphanumeric character, and/or may include another physical attribute that permits the marker to be distinguished relative to another marker in the radiological scan, which in turn permits each marker, of the plurality of markers, to identify a particular portion of the surgical margin relative to other portions of the surgical margin in the radiological scan. In this way, it is possible to individually mark each of the portions of a surgical margin of a surgical cavity to properly identify each portion of the surgical margin in the radiological scan after a surgery.

FIG. 1 illustrates an example implementation 100 of a surgical cavity associated with a tumor resection, a biopsy, and/or the like. As shown in FIG. 1, implementation 100 may include a surgical cavity 102, a surgical margin 104 of surgical cavity 102, and a plurality of markers 106 (collectively referred to as "markers 106", and individually referred to as "marker 106").

In some implementations, surgical cavity 102 and surgical margin 104 may be part of a patient's body. In some implementations, surgical cavity 102 may include a three-dimensional cavity that results from a surgery performed on the patient, such as a surgery to remove a tumor or another type of an abnormal tissue. The surgery may include a partial mastectomy, a lumpectomy, a biopsy, and/or any other type of surgery where a surgical cavity is formed as a result of a body tissue being removed from the patient.

In some implementations, surgical margin 104 may include a portion of the patient's body tissue surrounding surgical cavity 102. Surgical margin 104 may function as a portion of the patient's body tissue that is to be used to determine whether the removal of the tumor was successful or whether the abnormal tissue associated with the tumor was completely removed. In this way, after surgical removal of the tumor, a practitioner may analyze surgical margin 104 to determine whether the abnormal tissue is present in surgical margin 104, which may indicate that not all of the abnormal tissue was removed, and that another resection is needed in order to remove the abnormal tissue in surgical margin 104.

In some implementations, the size of surgical margin 104 (e.g., the thickness of body tissue in millimeters or another unit of measurement) may be determined by a medical practitioner, by a computing device, based on various medical practices, and/or the like. As an example, surgical margin 104 may be about 1 mm in thickness, about 2 mm in thickness, and/or the like.

In some implementations, surgical margin 104 may include various portions, such as an anterior portion (e.g., a portion of surgical margin 104 that is adjacent to a front portion of surgical cavity 102), a posterior portion (e.g., a portion of surgical margin 104 that is adjacent to a rear portion of surgical cavity 102), a lateral portion (e.g., a portion of surgical margin 104 that is adjacent to a side portion of surgical cavity 102), a medial portion (e.g., a portion of surgical margin 104 that is adjacent to a middle portion of surgical cavity 102), a superior portion (e.g., a portion of surgical margin 104 that is adjacent to a top portion of surgical cavity 102), an inferior portion (e.g., a portion of surgical margin 104 that is adjacent to a bottom portion of surgical cavity 102), and/or the like.

Markers 106 may be attached to the patient's body in surgical margin 104 to identify a particular portion of surgical margin 104 relative to other portions of surgical margin 104. Additionally, or alternatively, markers 106 may be attached and/or implanted in surgical cavity 102 to identify a particular portion of surgical cavity 102 relative to other portions of surgical cavity 102. In the implementations described herein, descriptions of attaching markers 106 to surgical margin 104 may also be applied to attaching markers 106 to surgical cavity 102.

Markers 106 may include a first element 108 to attach a marker 106 to surgical margin 104, and a second element 110 attached to first element 108. Second element 110 may include an indicator 112 for uniquely identifying a portion of surgical margin 104 through a radiological scan, such as a CT scan, an X-ray scan, and/or the like. In some implementations, first element 108 may be an integral part of second element 110, such that first element 108 and second element 110 are a single piece. In some implementations, first element 108 may be a separate piece from second element 110 and may be removably or irremovably attachable to second element 110.

In some implementations, indicator 112 of second element 110 may include an alphanumeric character representing the portion being identified by marker 106 (e.g., the letter "M" for a medial portion, the letter "L" for a lateral portion, the number "1" for a medial portion, the number "2" for a lateral portion, and/or the like), may include a particular shape (e.g., a circle for an inferior portion, a square for a superior portion, and/or the like), may include a particular symbol, may include a particular material (e.g., titanium for an anterior portion, an alloy or a composite material for a posterior portion, and/or the like), and/or another physical indicator that may be used to identify a portion of surgical margin 104 through a radiological scan and distinguish one portion from another portion. In some implementations, indicator 112 may be directly attached to first element 108 such that, in a side view of marker 106 that shows indicator 112, at least a portion of indicator 112 is in a direct contact with the body tissue of the patient and/or surgical margin 104.

In some implementations, each particular marker 106 may include a unique indicator such that each particular marker 106 may be distinguished from other markers 106 in a radiological scan. For example, a first marker 106 may have a different alphanumeric character relative to a second marker 106, first marker 106 may have a different shape relative to second marker 106, first marker 106 may have a different symbol relative to second marker 106, first marker 106 may have a different material relative to second marker 106, and/or the like.

In some implementations, the material of indicator 112 of second element 110 may differ from a material of a remaining portion of marker 106, such that, throughout an entirety of marker 106, only indicator 112 may be detectable by the radiological scan. In some implementations, the material of indicator 112 may differ from a material of the remaining portion of marker 106, such that, throughout the entirety of marker 106, indicator 112 is more visible in the radiological scan relative to the remaining portion of marker 106. The material of marker 106, or only indicator 112, may be titanium or other safe materials for a body that can be detected by the radiological scan. The remaining portions of marker 106, which do not include titanium, for example, may include another material that can be dissolved and absorbed by the body after a certain period of time. The other material may also be safe for a body and may include a polymer, a gel, and/or the like, that may not be detected by the radiological scan.

In this way, during a surgery, operation, procedure, and/or the like, in which a tumor and/or abnormal tissue is removed from a body of a patient, the removal of the tumor and/or abnormal tissue may cause surgical cavity 102 to be formed in the patient's body. Prior to closing surgical cavity 102, a practitioner (e.g., a surgeon and/or the like), a medical device, and/or the like, may insert one or more markers 106 into surgical cavity 102 and attach each marker 106, of the one or more markers, to a particular portion of surgical margin 104 surrounding surgical cavity 102. Once the one or more markers 106 are attached to surgical margin 104, the practitioner and/or medical device may close surgical cavity 102. Accordingly, the practitioner, another practitioner (e.g., a radiologist and/or the like), a medical device, and/or the like may capture a radiological scan of the area of the patient's body in which surgical cavity 102 and surgical margin 104 are located, may identify the one or more markers 106 in the radiological scan, and may locate the various portions of surgical margin 104 based on identifying the one or more markers 106 in the radiological scan. In this way, the practitioner(s) and/or the medical device may more accurately and quickly identify surgical margin 104 and analyze surgical margin 104 for the abnormal tissue, which improves treatment of various types of tumors and/or abnormal tissue. For example, a radiation oncology practitioner may plan radiation treatment to target rays of radiation on the tissue identified by the one or more markers 106 in the radiological scan.

As indicated above, FIG. 1 is provided merely as an example. Other examples are may differ from what is described with regard to FIG. 1.

Figure 2A:
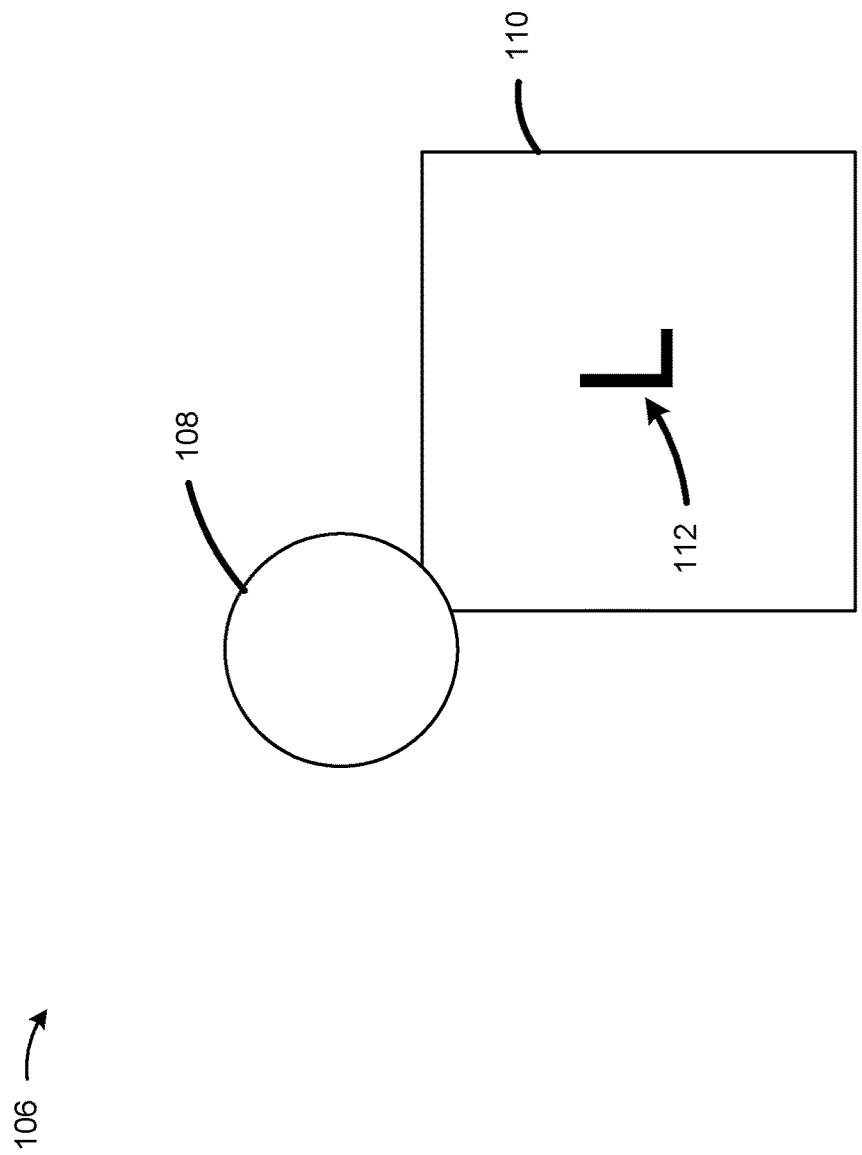
FIGS. 2A and 2B are illustrations of an example marker for identifying portions of a surgical margin of a surgical cavity.
Figure 2B:
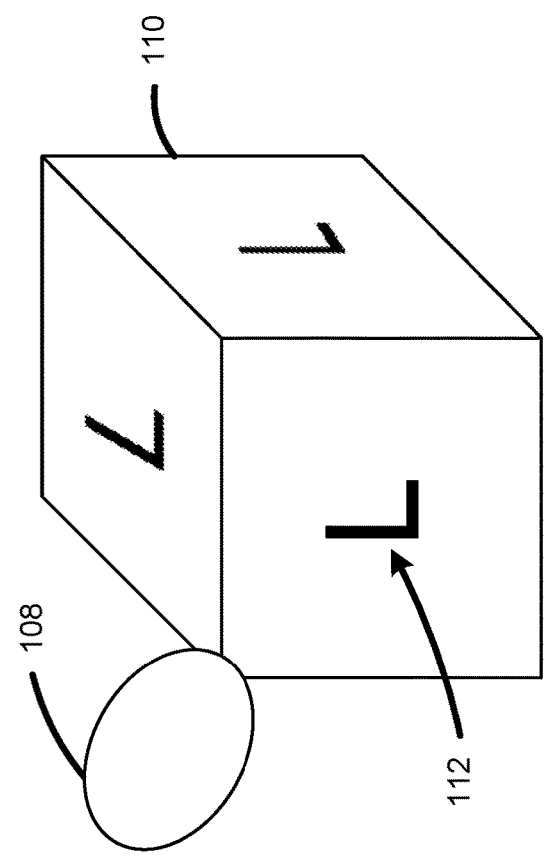

FIGS. 2A and 2B illustrate a detailed view of an example marker 106. FIG. 2A may illustrate a two-dimensional view of marker 106 and FIG. 2B may illustrate a three-dimensional view of marker 106. As shown in FIG. 2A, marker 106 may include a hollow portion for first element 108. The hollow portion may be configured to pass a thread such that marker 106 may be stitched, using the thread, to a body tissue. In this way, marker 106 may be stitched to a portion of surgical margin 104. In some implementations, the opening of the hollow portion may be of various sizes and shapes, which may depend on the size of marker 106, the size of the thread being used to attach marker 106 to the portion of surgical margin 104, and/or the like. In some implementations, the size and/or shape of the opening of the hollow portion may be configured based on a particular context in which marker 106 is used.

As shown in FIG. 2B, second element 110 may include a three-dimensional shape, such as a cube, a sphere, a cylinder, a cone, and/or the like. For example, second element 110 may include a plurality of surfaces, such as a first surface, a second surface opposing the first surface, a third surface, and a fourth surface opposing the third surface (the third surface and the fourth surface being located between the first surface and the second surface), and a fifth surface and a sixth surface each being placed adjacent to each of the first surface, the second surface, the third surface, and the fourth surface. In some implementations, indicator 112 may include indicia placed on each of a plurality of surfaces of second element 110. For example, and as shown in FIG. 2B, indicator 112 may include the alphanumeric character "L" placed on each surface, of the plurality of surfaces, of second element 110.

In some implementations, a material of the second element 110 may cause one or more surfaces (and the indicia located thereon), of the plurality of surfaces, of second element 110 to be more visible or prominent in a radiological scan relative to one or more other surfaces (and the indicia located thereon), of the plurality of surfaces, of second element 110. In some implementations, a material of the indicia on each of the first surface, the second surface, the third surface, the fourth surface, and the fifth surface may be different from a material of the indicia in the remaining surfaces of the first surface, the second surface, the third surface, the fourth surface, and the fifth surface, such that the indicia on each of the first surface, the second surface, the third surface, the fourth surface, and the fifth surface exhibit different levels of visibility and/or prominence in a radiological scan. In some implementations, the indicia may include a first material disposed on a first surface, of the plurality of surfaces, of second element 110 and a second material disposed on a second surface, of the plurality of surfaces of second element 110, such that the first material is more (or less) visible and/or prominent in a radiological scan relative to the second material.

As indicated above, FIGS. 2A and 2B are provided merely as an example. Other examples are may differ from what is described with regard to FIGS. 2A and 2B.

Figure 3A:
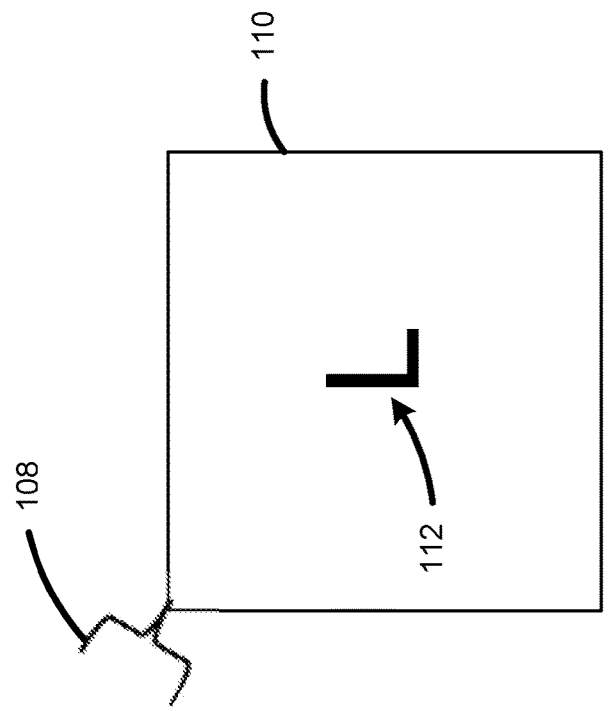
FIGS. 3A and 3B are illustrations of an example marker for identifying portions of a surgical margin of a surgical cavity.
Figure 3B:
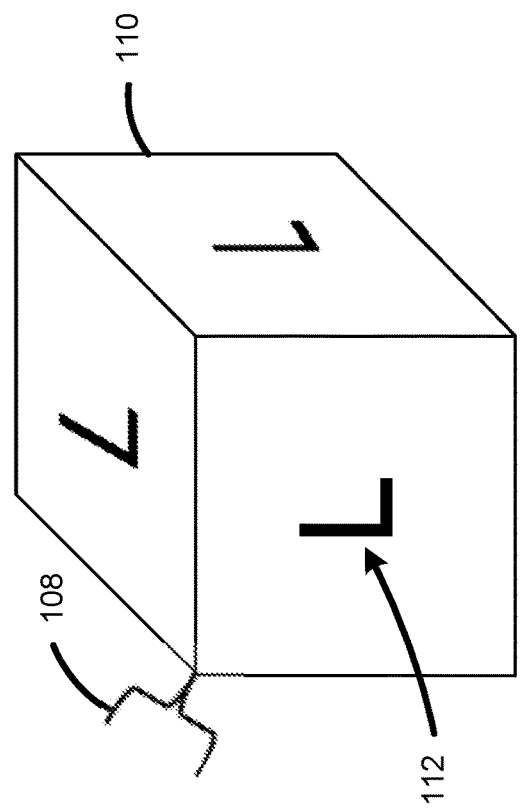

FIGS. 3A and 3B illustrate a detailed view of a marker 106. FIG. 3A may illustrate a two-dimensional view of marker 106 and FIG. 3B may illustrate a three-dimensional view of marker 106. As shown in FIG. 3A, marker 106 may include a protrusion for first element 108. In some implementations, marker 106 may include a plurality of protrusions for first element 108. The protrusion may be barbed and/or may project from second element 110 and may penetrate into a body tissue of a patient. In this way, the protrusion may reversibly or irreversibly deform to attach marker 106 to a portion of a surgical margin 104.

As shown in FIG. 3B, second element 110 may include a three-dimensional shape, such as a cube, a sphere, a cylinder, a cone, and/or the like. For example, second element 110 may include a plurality of surfaces, such as a first surface, a second surface opposing the first surface, a third surface, and a fourth surface opposing the third surface (the third surface and the fourth surface being located between the first surface and the second surface), and a fifth surface and a sixth surface each being placed adjacent to each of the first surface, the second surface, the third surface, and the fourth surface. In some implementations, indicator 112 may include indicia placed on each of a plurality of surfaces of second element 110. For example, and as shown in FIG. 3B, indicator 112 may include the alphanumeric character "L" placed on each surface, of the plurality of surfaces, of second element 110.

In some implementations, a material of the second element 110 may cause one or more surfaces (and the indicia located thereon), of the plurality of surfaces of second element 110 to be more visible or prominent in a radiological scan relative to one or more other surfaces (and the indicia located thereon), of the plurality of surfaces of second element 110. In some implementations, a material of the indicia on each of the first surface, the second surface, the third surface, the fourth surface, and the fifth surface may be different from a material of the indicia in the remaining surfaces of the first surface, the second surface, the third surface, the fourth surface, and the fifth surface, such that the indicia on each of the first surface, the second surface, the third surface, the fourth surface, and the fifth surface exhibit different levels of visibility and/or prominence in a radiological scan. In some implementations, the indicia may include a first material disposed on a first surface of the plurality of surfaces of second element 110, and a second material disposed on a second surface of the plurality of surfaces of second element 110, such that the first material is more (or less) visible and/or prominent in a radiological scan relative to the second material.

As indicated above, FIGS. 3A and 3B are provided merely as an example. Other examples may differ from what is described with regard to FIGS. 3A and 3B.

While first element 108 is illustrated as a hollow portion in FIGS. 2A and 2B, and a protrusion in FIGS. 3A and 3B, first element 108 may include another type or configuration of attachment device and/or method for attaching marker 106 to a portion of surgical margin 104. For example, first element 108 may include various attachment means, such as clips, staples, hooks, adhesives, and/or the like.

Figure 4:
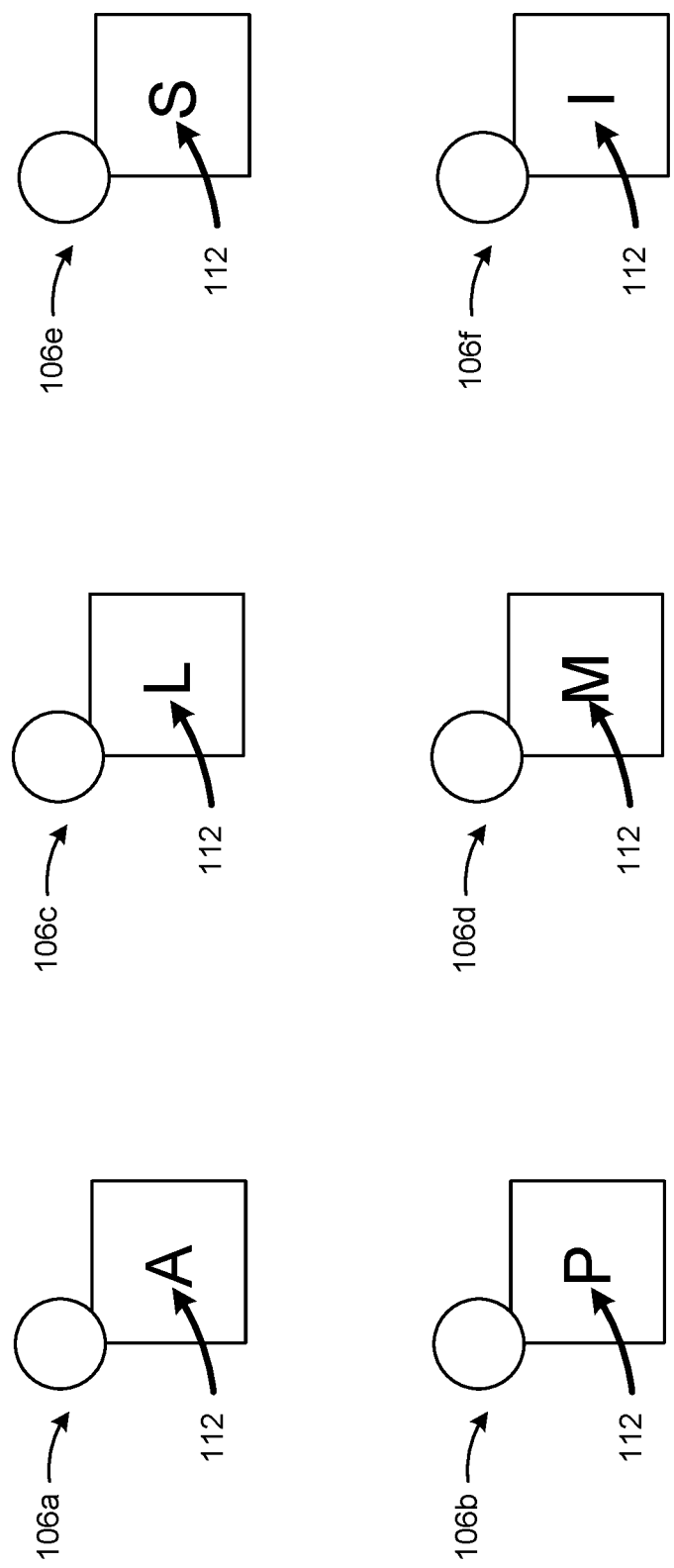
FIG. 4 is an illustration of an example plurality of markers for identifying portions of a surgical margin of a surgical cavity.

FIG. 4 illustrates an example plurality of markers (e.g., markers 106a-106e, individually referred to as "marker 106", and collectively referred to as "markers 106") for identifying portions of a surgical margin of a surgical cavity. As shown in FIG. 4, each marker 106 may include a different indicator 112, for individually, independently, and/or uniquely identifying a particular portion, of a plurality of portions, of a surgical margin associated with a surgical cavity located in a body of a patient. For example, marker 106a may include an indicator 112 associated with an anterior portion of the surgical margin (e.g., the alphanumeric character "A"), marker 106b may include an indicator 112 associated with a posterior portion of the surgical margin (e.g., the alphanumeric character "P"), marker 106c may include an indicator 112 associated with a lateral portion of the surgical margin (e.g., the alphanumeric character "L"), marker 106d may include an indicator 112 associated with a medial portion of the surgical margin (e.g., the alphanumeric character "M"), marker 106e may include an indicator 112 associated with a superior portion of the surgical margin (e.g., the alphanumeric character "S"), marker 106f may include an indicator 112 associated with an inferior portion of the surgical margin (e.g., the alphanumeric character "I"), and/or the like.

Each of markers 106 may be designed and patterned with a different alphanumeric character, a different color, and/or a different material to be applied to a specific portion of a surgical margin among the anterior, posterior, lateral, medial, superior, and inferior portions such that a radiological scan distinguishes a marker 106 from other markers 106 located in the surgical margin.

In some implementations, an automatic dispenser may dispense the markers 106. For example, the automatic dispenser may be a stapler, a ligating clip dispenser, an endoscopic clip applier, and/or the like. In some implementations, the automatic dispenser may, upon activation by a user, attach the first element 108 to tissue (e.g., surgical cavity 102 and/or the like), thereby attaching marker 106 to the tissue.

In some implementations, the automatic dispenser may include a selection mechanism permitting a user to select indicator 112 for marker 106 each time the that the automatic dispenser dispenses marker 106. For example, the selection mechanism may include a rotating knob, one or more buttons, a touchscreen, and/or the like for the user to select indicator 112 for the next marker 106 dispensed by the automatic dispenser. In some implementations, a user may manipulate the selection mechanism to select a marker 106 bearing a chosen indicator 112, and activate the automatic dispenser to attach the selected marker 106 to tissue (e.g., surgical cavity 102 and/or the like).

In some implementations, markers 106 may be designed and patterned with a different alphanumeric character, a different color, and/or a different material, as described herein, before markers 106 are fed, loaded, and/or the like into the automatic dispenser. For example, before markers 106 are placed in the automatic dispenser, indicators 112 may be applied to markers 106 such that a radiological scan distinguishes a marker 106 from other markers 106 located in the surgical margin.

In some implementations, markers 106 may be sequentially fed, loaded, and/or the like into the automatic dispenser. For example, markers 106 corresponding to each of the anterior, posterior, lateral, medial, superior, and inferior portions may be sequentially arranged and fed into the automatic dispenser in an order such that, upon a sequence of activations of the automatic dispenser, the automatic dispenser dispenses markers 106 in the order.

Additionally, or alternatively, each type of marker 106 may be fed, loaded, and/or the like into the automatic dispenser separately and/or individually. For example, markers 106 corresponding to the anterior portion may be fed into the dispenser, and then markers 106 corresponding to the posterior portion may be fed into the dispenser, and/or the like. In some implementations, the user may manipulate the selection mechanism on the automatic dispenser to select a type of marker 106 for the automatic dispenser to dispense.

In some implementations, markers 106 may not include indicator 112 when markers 106 are fed, loaded, and/or the like into the automatic dispenser, and the automatic dispenser may apply a different alphanumeric character, a different color, and/or a different material to markers 106 such that a radiological scan distinguishes a marker 106 from other markers 106. For example, the automatic dispenser may include a pressing device, an imprinting device, an engraving device, an injection device, an indicia-providing device, and/or the like for applying indicator 112 to markers 106.

In some implementations, the automatic dispenser may apply a different alphanumeric character, a different color, and/or a different material to one or more sides, surfaces, and/or the like of markers 106. For example, the automatic dispenser may apply indicator 112 to adjacent surfaces, opposite surfaces, selected surfaces, all surfaces, and/or the like of markers 106. In some implementations, the automatic dispenser may apply a same indicator 112 to multiple surfaces of markers 106. Additionally, or alternatively, the automatic dispenser may apply a different indicator 112 to multiple surfaces of markers 106 (e.g., a different indicator 112 on each surface, a first indicator 112 on two surfaces and a second indicator 112 on two other surfaces, and/or the like).

In some implementations, the user may manipulate the selection mechanism on the automatic dispenser to select a type of marker 106, and the automatic dispenser may apply an alphanumeric character, a different color, and/or a different material to a marker 106. For example, the automatic dispenser may receive the user selection of an indicator 112, apply the indicator 112 to marker 106 upon activation by the user, and attach marker 106 to tissue (e.g., surgical cavity 102 and/or the like).

As indicated above, FIG. 4 is provided merely as an example. Other examples are may differ from what is described with regard to FIG. 4.

Figure 5:
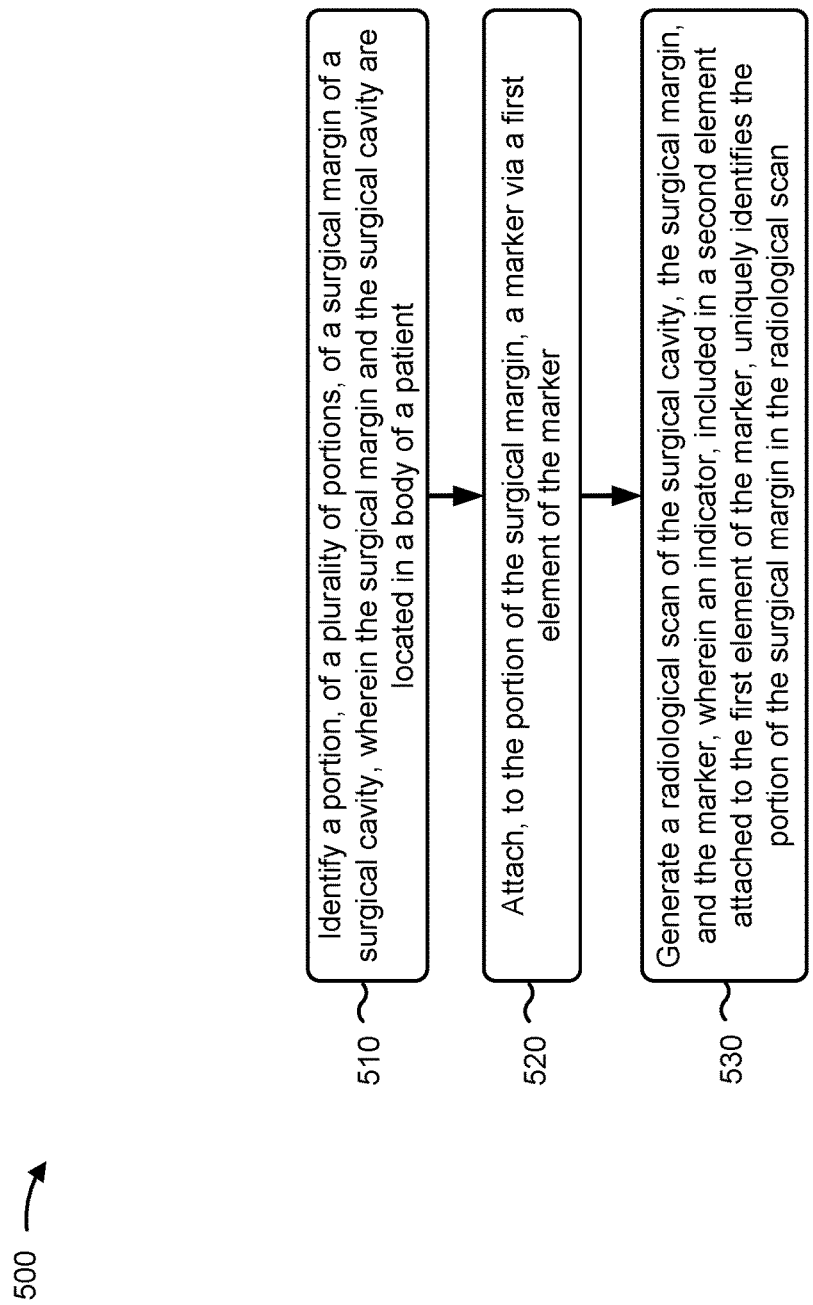
FIG. 5 is a flow chart of an example process for identifying portions of a surgical margin of a surgical cavity.

FIG. 5 is a flow chart of an example process 500 for identifying portions of a surgical margin of a surgical cavity. In some implementations, one or more process blocks of FIG. 5 may include the use of a marker (e.g., marker 106). In some implementations, one or more process blocks of FIG. 5 may include the use of another device or a group of devices separate from or including the marker.

As shown in FIG. 5, process 500 may include identifying a portion, of a plurality of portions, of a surgical margin of a surgical cavity, wherein the surgical margin and the surgical cavity are located in a body of a patient (block 510). For example, a portion, of a plurality of portions, of a surgical margin of a surgical cavity may be identified, as described above. In some implementations, the surgical margin and the surgical cavity are located in a body of a patient.

As further shown in FIG. 5, process 500 may include attaching, to the portion of the surgical margin, a marker via a first element of the marker (block 520). For example, a marker may be attached to the portion of the surgical margin via a first element of the marker, as described above. In some implementations, process 500 may include implanting, into the portion of the surgical margin, a marker via a first element of the marker.

As further shown in FIG. 5, process 500 may include generating a radiological scan of the surgical cavity, the surgical margin, and the marker, wherein an indicator, included in a second element attached to the first element of the marker, uniquely identifies the portion of the surgical margin in the radiological scan (block 530). For example, a radiological scan of the surgical cavity, the surgical margin, and the marker, may be generated, as described above. In some implementations, an indicator, included in a second element attached to the first element of the marker, uniquely identifies the portion of the surgical margin in the radiological scan.

Process 500 may include additional implementations, such as any single implementation or any combination of implementations described below and/or described with regard to any other process described herein. Although FIG. 5 shows example blocks of process 400, in some implementations, process 500 may include additional blocks, fewer blocks, different blocks, or differently arranged blocks than those depicted in FIG. 5. Additionally, or alternatively, two or more of the blocks of process 500 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A marker, comprising:
   a first element to attach the marker to a portion of a plurality of portions of a surgical margin of a surgical cavity located in a body of a patient; and
   a second element attached to the first element,
      wherein the second element comprises a plurality of surfaces each including an indicator to uniquely identify the portion, of the plurality of portions of the surgical margin, in the body of the patient through a radiological scan,
      wherein the indicator included in each of the plurality of surfaces comprises at least one of an alphanumeric character, a shape, or a symbol,
      wherein the indicator for each of the plurality of surfaces is the same on each of the plurality of surfaces, and
      wherein only a material of the indicator on each of the plurality of surfaces is detectable by a radiological ray in a targeted radiation.

2. The marker of claim 1, wherein the plurality of portions of the surgical margin comprises at least one of:
   an anterior portion,
   a posterior portion,
   a lateral portion,
   a medial portion,
   a superior portion, or
   an inferior portion; and
   wherein at least one of:
   the marker comprises an additional lettering based on a type of a tumor and a location of surgery, or
   the marker is configured to mark a specific location of the surgical margin as a target of radiation or therapy.

3. The marker of claim 1, wherein the indicator is to:
   identify a location of the portion of the plurality of portions of the surgical margin, or
   mark a specific location of the surgical margin as a target of radiation or therapy.

4. The marker of claim 1, wherein the indicator is to distinguish, in the body of the patient, the portion of the plurality of portions of the surgical margin relative to another portion of the plurality of portions of the surgical margin.

5. The marker of claim 1,
   wherein the first element is a staple that is configured to irreversibly deform to attach the marker to the portion of the plurality of portions of the surgical margin.

6. The marker of claim 1, wherein the indicator is to be visible in the radiological scan.

7. The marker of claim 1, wherein, through the radiological scan in the body of the patient, the indicator is to:
  identify the portion of the plurality of portions of the surgical margin, or
  mark a specific location of the surgical margin as a target of therapy differently from another portion of the plurality of portions of the surgical margin that is embedded with another marker.

8. The marker of claim 1, wherein the first element is a staple that attaches the marker to the portion of the plurality of portions of the surgical margin.

9. The marker of claim 1, wherein the indicator is located on the plurality of surfaces of the second element such that the indicator is visible in multiple directions of the radiological scan with regard to an exposed surface of the plurality of surfaces of the second element to radiological rays, and
  wherein another surface, of the plurality of surfaces of the second element, faces an opposite direction from the exposed surface of the plurality of surfaces of the second element.

10. A marker, comprising:
  a first element to attach the marker to a portion of a plurality of portions of a surgical margin of a surgical cavity located in a body of a patient; and
  a second element attached to the first element,
    wherein the first element comprises a protrusion projecting from the second element,
    wherein the protrusion is to penetrate into a body tissue of the body of the patient,
    wherein the protrusion is to irreversibly deform to attach the marker to the body tissue,
    wherein the second element comprises a plurality of surfaces each including an indicator to uniquely identify the portion, of the plurality of portions of the surgical margin, in the body of the patient through a radiological scan, and
    wherein only a material of the indicator on each of the plurality of surfaces is detectable by a radiological ray in a targeted radiation.

11. A marker, comprising:
  a main body comprising a plurality of surfaces that each have an indicator for uniquely distinguishing a portion of a surgical cavity, in a body of a patient, from remaining portions of the surgical cavity,
    wherein the indicator of each of the plurality of surfaces is the same,
    wherein, in a radiological scan of a targeted radiation, a remaining portion of the main body, other than the indicator, has a different shape than the indicator,
    wherein the indicator is detectable in the radiological scan and the remaining portion is less detectable in the radiological scan relative to the indicator, and
    wherein a material of the indicator that is disposed on each of the plurality of surfaces is different from a material of the remaining portion, and
  an element, attached to the main body, configured to deform to connect the marker to the portion of the surgical cavity.

12. The marker according to claim 11, wherein the element is configured to staple to the portion, of the surgical cavity, to attach the marker to the portion of the surgical cavity.

13. The marker according to claim 11, wherein the indicator is visible in multiple directions of the radiological scan with regard to an exposed surface of the plurality of surfaces of the main body to radiological rays, and
  wherein another surface, of the plurality of surfaces of the main body, faces an opposite direction from the exposed surface of the plurality of surfaces of the main body.

14. The marker according to claim 13, wherein the plurality of surfaces of the main body further comprise:
  an intervening surface located between the exposed surface of the plurality of surfaces of the main body and the other surface of the plurality of surfaces of the main body.

15. The marker according to claim 14, wherein the intervening surface extends from the exposed surface of the plurality of surfaces of the main body to the other surface of the plurality of surfaces of the main body.

16. The marker according to claim 14, wherein the plurality of surfaces of the main body further comprise:
  another intervening surface located between the exposed surface of the plurality of surfaces of the main body and the other surface of the plurality of surfaces of the main body,
  and
  wherein the indicator of each of the exposed surface, the other surface, the intervening surface, and the other intervening surface is visible in multiple directions of the radiological scan to radiological rays.

17. The marker according to claim 11, wherein, through the radiological scan of the body of the patient, the indicator is to uniquely identify a location of a margin of the surgical cavity with respect to remaining margins of the surgical cavity, other than the margin of the surgical cavity, which are embedded with different markers than the marker.

18. The marker of claim 11, wherein, through the radiological scan of the body of the patient, the indicator is to:
  identify a location of a margin of the surgical cavity with respect to remaining margins of the surgical cavity, or
  mark the location of the margin as a target of radiation or therapy.

19. A plurality of markers, each marker of the plurality of markers comprising:
  a main body attached to a deformable element that is configured to connect to a portion of a plurality of portions of a surgical margin of a surgical cavity located in a body of a patient,
  wherein the main body comprises:
    an indicator to uniquely identify the portion of the plurality of portions of the surgical margin through a radiological scan in a targeted radiation in the body of the patient,
    wherein the indicator of a marker of the plurality of markers is different from the indicator of another marker of the plurality of markers to distinguish the marker from the other marker in the radiological scan,
    wherein surfaces of the main body of the marker each have a first pattern, surfaces of the main body of the other marker each have a second pattern, and the first pattern is different from the second pattern, and
    wherein, throughout an entirety of the plurality of markers, only a material of the indicator of each marker is detectable by a radiological ray in the targeted radiation.

20. The plurality of markers of claim 19, wherein the indicator of the marker is to:

distinguish the portion of the plurality of portions of the surgical margin relative to another portion of the plurality of portions of the surgical margin identified by the indicator of the other marker, or mark a specific location as a target of radiation or therapy.

21. The plurality of markers of claim 19, wherein, through the radiological scan of the body of the patient, the indicator of each marker is to:

identify a location of the surgical margin of the surgical cavity with respect to remaining margins of the surgical cavity, or mark a specific location as a target of radiation or therapy, and wherein remaining markers of the plurality of markers are configured to be embedded in the remaining margins of the surgical cavity based on differences between the indicator of each marker and the indicators of the remaining markers of the plurality of markers.

22. The plurality of markers of claim 19, wherein the indicator of the marker comprises:

a first alphanumeric character, associated with the portion of the plurality of portions of the surgical margin, to mark a specific location as a target of radiation or a therapy, the first alphanumeric character being placed on each of the surfaces of the main body of the marker, wherein the indicator of the other marker comprises a second alphanumeric character, associated with another portion of the plurality of portions of the surgical margin, to mark the specific location to be the target of radiation or therapy, the second alphanumeric character being placed on each of the surfaces of the main body of the other marker, and wherein the first alphanumeric character and the second alphanumeric character are different alphanumeric characters.

23. The plurality of markers according to claim 19, wherein the indicator of the marker comprises at least one of:

an alphanumeric character, a shape, or a symbol.

24. The plurality of markers according to claim 19, wherein the indicator of the marker includes a different symbol from the indicators of remaining markers of the plurality of markers.

25. The plurality of markers according to claim 19, wherein the indicator of the marker includes a different alphabetical letter from the indicators of remaining markers of the plurality of markers.

26. The plurality of markers according to claim 19, wherein the indicator of the marker includes a different shape from the indicators of remaining markers of the plurality of markers.

27. The plurality of markers of claim 19, wherein the main body of each marker of the plurality of markers is a cube, a cylinder, or a cone.

28. A plurality of markers, each marker of the plurality of markers comprising:

a main body comprising:

a plurality of surfaces each including an indicator to:

identify a portion of a surgical margin, or mark a specific location as a target of radiation or therapy, wherein the indicator of a marker of the plurality of markers is different from another indicator of another marker of the plurality of markers to distinguish the marker from the other marker in a radiological scan of the surgical margin, wherein the main body of the marker is completely detached from, and is structurally independent from, the main body of the other marker, and wherein, throughout an entirety of the plurality of markers, only a material of the indicator of each marker is detectable by a radiological ray in a targeted radiation.

29. The plurality of markers of claim 28, wherein each marker of the plurality of markers further comprises:

an element, attached to the main body, configured to:

deform to connect the marker to the portion of the surgical margin, or mark the specific location as the target of radiation or therapy, wherein the element is configured to staple to the portion of the surgical margin to attach the marker to the portion of the surgical margin.

* * * * *